United States Patent
Kim et al.

(10) Patent No.: US 11,614,441 B2
(45) Date of Patent: Mar. 28, 2023

(54) METHOD FOR ASSESSING VALIDITY OF CELL THERAPY PRODUCT

(71) Applicants: KOLON LIFE SCIENCE, INC., Seoul (KR); KOLON TISSUEGENE, INC., Rockville, MD (US)

(72) Inventors: Su Jeong Kim, Seoul (KR); Sang Eun Noh, Incheon (KR); Jun Ho Lee, Seoul (KR); Hyeon Youl Lee, Gyeonggi-do (KR); Kyoung Baek Choi, Incheon (KR); Heon Sik Choi, Seoul (KR)

(73) Assignees: KOLON LIFE SCIENCE, INC., Seoul (KR); KOLON TISSUEGENE, INC., Rockville, MD (US)

( * ) Notice: Subject to any disclaimer, the term of this patent is extended or adjusted under 35 U.S.C. 154(b) by 478 days.

(21) Appl. No.: 16/627,541

(22) PCT Filed: Jun. 29, 2018

(86) PCT No.: PCT/KR2018/007438
§ 371 (c)(1),
(2) Date: Dec. 30, 2019

(87) PCT Pub. No.: WO2019/004795
PCT Pub. Date: Jan. 3, 2019

(65) Prior Publication Data
US 2020/0124590 A1    Apr. 23, 2020

(30) Foreign Application Priority Data

Jun. 30, 2017   (KR) .................. 10-2017-0083569

(51) Int. Cl.
| | | |
|---|---|---|
| *G01N 33/50* | (2006.01) | |
| *A01N 1/02* | (2006.01) | |
| *A61K 35/32* | (2015.01) | |
| *C12N 5/077* | (2010.01) | |
| *C12N 13/00* | (2006.01) | |
| *G01N 33/68* | (2006.01) | |

(52) U.S. Cl.
CPC ....... *G01N 33/5008* (2013.01); *A01N 1/0221* (2013.01); *A01N 1/0284* (2013.01); *A61K 35/32* (2013.01); *C12N 5/0655* (2013.01); *C12N 13/00* (2013.01); *G01N 33/68* (2013.01); *C12N 2501/15* (2013.01)

(58) Field of Classification Search
None
See application file for complete search history.

(56) References Cited

U.S. PATENT DOCUMENTS

| | | |
|---|---|---|
| 6,090,367 A | 7/2000 | Khalil |
| 2003/0175257 A1 | 9/2003 | Song et al. |
| 2003/0185809 A1 | 10/2003 | Song et al. |
| 2006/0188885 A1 | 8/2006 | Bodian et al. |
| 2010/0055080 A1 | 3/2010 | Song et al. |
| 2010/0303773 A1 | 12/2010 | Yang et al. |
| 2011/0229445 A1 | 9/2011 | Lee et al. |

FOREIGN PATENT DOCUMENTS

| | | |
|---|---|---|
| JP | 2016136159 A | 7/2016 |
| KR | 2000-0072904 A | 12/2000 |
| KR | 10-2005-0002898 A | 1/2005 |
| KR | 10-2005-0012226 A | 1/2005 |
| WO | WO 96/39196 A1 | 12/1996 |
| WO | WO 00/66177 A1 | 11/2000 |
| WO | WO 2016/126139 A1 | 8/2016 |
| WO | WO 2016/193591 A1 | 12/2016 |

OTHER PUBLICATIONS

Office action dated May 31, 2022 from Japan Intellectual Property Office in a counterpart Japanese Patent Application No. 2020-522654 (all the cited references are listed in this IDS.)(English translation is also submitted herewith.).
Wen-Cheng Lo, et al. "Preferential therapy for osteoarthritis by cord blood MSCs through regulation of chondrogenic cytokines" Biomaterials, 2013, vol. 34, pp. 4739-4748.
Choi, K. B. et al., "hChonJb#7 Cells (Chondrocytes Expressing TGF-b1) Reduced Pain in a Rat Osteoarthritis Mo del", Molecular Therapy, May 2013, vol. 21, Supplement 1, p. S56.
Search Report dated Jun. 28, 2021 from Singapore Patent Office in a counterpart Singapore Patent Application No. 11201913795S.
Chul-Won Ha et al., "Initial phase I safety of retrovirally transduced human hondrocytes expressing transforming growth factor-beta-1 in degenerative arthritis patients",Cytotherapy, Feb. 29, 2012, pp. 247-256, vol. 2012, No. 14.
Cherian J. J. et al., "Preliminary results of a phase II randomized study to determine the efficacy and safety of genetically engineered allogeneic human chondrocytes expressing TGF-β1 in patients with grade 3 chronic degenerative joint disease of the knee", Osteoarthr. Cartil., Jul. 16, 2015, pp. 2109-2118, vol. 23, No. 2015, Osteoarthristis Research Society International.
Office action dated Sep. 1, 2020 from Intellectual Property Office of Singapore in a counterpart Singapore Patent Application No. 11201913793S (all the cited references are listed in this IDS.).
Hytham S. Salem et al. "The Safety and Efficacy of a Novel Cell-Based Gene Therapy for Knee Osteoarthritis" Orthopaedic Surgery, Surgical Technology International vol. 35, pp. 1-7.

(Continued)

*Primary Examiner* — Robert J Yamasaki
(74) *Attorney, Agent, or Firm* — The PL Law Group, PLLC

(57) ABSTRACT

The present invention provides a method for evaluating effectiveness of a cell therapeutic agent. When using TGF-β and/or TSP-1 expression level(s) in: (a) a first population of transformed mammalian cells with TGF-β; and (b) a second population of untransformed mammalian cells with the same gene, respectively, as a criterion for determining effectiveness of a cell therapeutic agent, and whether or not expression thereof, it is possible to definitely determine the therapeutic efficacy of each cell therapeutic agent prior to initiation of the treatment. In addition, since use of a cell therapeutic agent without therapeutic effects is avoided, undesired procedures and side effects may not be entailed.

14 Claims, 9 Drawing Sheets

(56) References Cited

OTHER PUBLICATIONS

Certificate of Analysis "Short Tandem Repeat (STR) DNA Amplification and Analysis", www.bioreliance.com.
MFDS News, KFDA revokes KOLON Life Science's Invossa-K Inj, Ministry of Food and Drug Safety (MFDS), published May 25, 2019 (English translation of summary thereof is submitted herewith).
Korea Health Industry Development Institute, "Development of Invossa, degerative arthritis medicine, and follow-up pipeline", Final Evaluation Report of High-Tech Biopharmaceuticals Project for Global Market, Attachment 3 at p. 13, Jul. 2019 (Translation of Attachment 3 is submitted herewith).
Office action dated Dec. 27, 2019 from Korean Patent Office in a counterpart Korean Patent Application No. 10-2018-0075978 (all the cited references are listed in this IDS.).
European Search Report For 18823401.7 dated Jan. 27, 2021 from European patent office in a counterpart European patent application.
International Search Report for PCT/KR2018/007438 dated Feb. 8, 2019.
I-Ming Jou et al., "Thrombospondin 1 as an Effective Gene Therapeutic Strategy in Collagen-Induced Arthritis", Arthritis & Rheumatism, vol. 52, No. 1, pp. 339-344, 2005.
Lee KH et al., "Regeneration of hyaline cartilage by cell-mediated gene therapy using transfo~rming growth factor beta 1-producing fibroblasts.", Hum Gene Ther. vol. 12(14), pp. 1805-1813, 2001 (Abstract is submitted herewith.).
Sun U. Song et al., "Hyaline Cartilage Regeneration Using Mixed Human Chondrocytes and Transforming Growth Factor-β1-Producing Chondrocytes", Tissue Engineering, vol. 11, 2005 (Abstract is submitted herewith.).
Examination Report dated Feb. 23, 2022 from Australian Intellectual Property Office in a counterpart Australian Patent Application No. 2018290629 (all the cited references are listed in this IDS.).
Noh MJ, et al. "Pre-clinical studies of retrovirally transduced human chondrocytes expressing transforming growth factor-beta-1 (TG-C)" Cytotherapy. Jan. 1, 2010;12(3):384-93.
Yoon HJ, et al. "Type II collagen and glycosaminoglycan expression induction in primary human chondrocyte by TGF-β1" BMC Musculoskeletal Disorders. Dec. 2015;16(1):1-2.
Song SU, et al. "Regeneration of hyaline articular cartilage with irradiated transforming growth factor β1-producing fibroblasts" Tissue engineering. May 1, 2004;10(5-6):665-72.(Abstract is submitted herewith.).

TSP-1 (ELISA assay)

| Cell | TSP-1 (ng/1x10^5cells/24hrs) | | | Avg |
|---|---|---|---|---|
| | #1 | #2 | #3 | |
| 1st batch | 77.53 | 71.79 | 79.90 | 76.41 |
| 2nd batch | 172.92 | 143.03 | 170.96 | 162.30 |
| 3rd batch | 124.27 | 109.48 | 114.68 | 116.14 |

METHOD FOR ASSESSING VALIDITY OF CELL THERAPY PRODUCT

TECHNICAL FIELD

The present invention relates to a method for evaluating effectiveness of a cell therapeutic agent and a method for manufacturing an osteoarthritis therapeutic agent.

BACKGROUND ART

Osteoarthritis, also called degenerative arthritis, is a chronic disease that causes a damage to joint cartilage, underlying bone and ligaments, and inflammation and pain due to cartilage damage or degenerative changes. The osteoarthritis occurs in almost all joints in the body, including fingers, knees (knee joints, patella), hips (hip joints, coxa), backs (lumbar joints), and neck (cervical joints). The cause of osteoarthritis has not been clearly investigated, but it is known to occur due to complex causes such as an age, genetic predisposition, external injury, and environmental effects. In the past, since an occurrence of osteoarthritis is related to the age, it has been thought to be caused by overuse of joints or cartilage wear due to aging. However, as various substances (cytokines, degrading enzymes, etc.) involved in cartilage metabolism have been disclosed, it is understood that these substances cause abnormalities in chondrocyte metabolism and inflammatory immune responses, and the like to damage the cartilage by various causes.

Major symptoms of the osteoarthritis include repeated pains, joint stiffness, reduced mobility and a loss of function. In general, the symptoms progress gradually over years. As the disease progresses to some extent, a surface of the joint becomes irregular due to the loss and degeneration of articular cartilage, thereby causing an increase in a degree of pain, and progressive movement disorder may lead to significant disruption to daily life. Further, joint deformation may also be caused. Currently, studies to target modulators and biochemical factors associated with cartilage growth are underway. These factors include, for example, bone morphogenic protein (BMP), which is an effective stimulant of bone formation, and a transforming growth factor beta (TGF-β), which stimulates cell growth and extracellular matrix (ECM) formation. In particular, TGF-β is known to be involved in proteoglycan synthesis, chondrocyte growth and tissue regeneration. Further, the TGF-β is also known to have immunosuppressive and anti-inflammatory functions. Indeed, other growth factors such as epidermal growth factor (EGF), insulin-like growth factor I (IGF-I), and basic fibroblast growth factor (bFGF) also stimulate cartilage regeneration, but these growth factors have no effect on cartilage damage.

Such growth factors as described above entail difficulties of administration in determining a concentration, release rate, delivery method, or the like at the time of administration. The researchers have continued to make efforts to deliver these factors through liposomes or by dissolving in medium, based on results proved in animal experiments. However, application of these factors to a human being has yet to be greatly improved.

The use of genetically modified chondrocytes is a novel technique that has successfully established cartilage regeneration in combination with cell-mediated gene therapy (Lee K H et al., Hum Gene Ther 2001; 12: 1805-1813, SUN U. SONG et al. Tissue Engineering 2005; 11: 1516-1526). This method uses a combination of allogeneic human chondrocytes transduced by a retroviral vector having TGF-β gene and allogeneic normal chondrocytes. This method can induce cartilage regeneration while minimizing surgical procedures.

Meanwhile, in a case of a cell therapeutic agent that produces and provides living cells, differences may occur in pharmaceutical products due to changes in production conditions such as a change of medium and work environment such as a temperature. Therefore, it is essential that quality control standards are established to ensure whether effectiveness (i.e., therapeutic efficacy) has been achieved at a level practically applicable to a patient in the production of cell therapeutic agents. However, it is a very difficult step to acquire consistent procedures and techniques to verify that the cell therapeutic agents have reliable therapeutic efficacy. Therefore, it is absolutely necessary to establish a method and a standard for properly verifying effectiveness of each cell therapeutic agent.

DISCLOSURE

Technical Problem

Under these circumstances, the present inventors have made efforts to develop a method for evaluating effectiveness of a cell therapeutic agent for specific diseases, in particular, osteoarthritis, and thus to establish a manufacturing process of an osteoarthritis therapeutic agent with excellent effects. As a result, the present inventors have found that, if a recombinant cell transformed so as to express TGF-β protein has an expression level of TGF-β over a specific level, it was confirmed that the cell therapeutic agent had significant effects in treatment of osteoarthritis. Further, the present inventors have also confirmed that, when untransformed cells have an expression level of thrombospondin 1 (TSP-1) over a specific level, the cell therapeutic agent also have significant effects in treatment of osteoarthritis. On the basis of the finding, the present invention has been completed.

Accordingly, an object of the present invention is to provide a method for evaluating effectiveness of a cell therapeutic agent.

Further, another object of the present invention is to provide a manufacturing process of a novel osteoarthritis therapeutic agent.

Technical Solution

Hereinafter, the present invention will be described in more detail.

According to an aspect of the present invention, there is provided a method for evaluating effectiveness of a cell therapeutic agent, which includes:

(1) preparing (a) a first population of transformed mammalian cells with a transforming growth factor beta (TGF-β), and (b) a second population of untransformed mammalian cells with the same gene, respectively;

(2) filling the first and second populations in step (1) into vials;

(3) inactivating the first population in step (2);

(4) culturing the first population in step (3);

(5) measuring expression quantity of TGF-β from the first population in step (4); and (6) evaluating effectiveness (i.e., therapeutic efficacy) of a cell composition as a therapeutic agent based on the TGF-β concentration measured in step (5), wherein, if an expression level of TGF-β is 0.65 ng/10$^5$ cells/24 hours or more in step (6), it is determined that the cell composition is effective as a therapeutic agent.

In this regard, the first population is transformed cells with TGF-β and has modified genetic trait. In order to prevent unexpected situation and ensure safety when such cells with modified genetic trait are to be provided as medicines, it is preferable to perform an inactivation process (for example, irradiation) such that the cells become in replication incompetent state. However, such an inactivation process affects TGF-β secretion and cells in situ, and therefore, a criterion for determining whether or not the cells are effective as a therapeutic agent even after inactivation will be essentially required.

Thus, a major characteristic of the present invention is to determine effectiveness of a cell composition as a cell therapeutic agent by identifying quality of the first population based on TGF-β expression level in the first population among the cell therapeutic agents (mixed cells) including: the first population of transformed mammalian cells with TGF-β; and the second population of untransformed mammalian cells with the same gene.

In the present invention, cells or cell groups included in the first population of mammalian cells transformed with TGF-β are preferably cells or cell groups expressing TGF-β1.

In the present invention, as a criterion for determining the effectiveness of the cell therapeutic agent of the present invention, a TGF-β expression level in the first population is not particularly limited as far as desired effects are achieved, however, is preferably at least 0.65 ng/10$^5$ cells/24 hours, more preferably at least 1.0 ng/10$^5$ cells/24 hours and, most preferably at least 1.7 ng/10$^5$ cells/24 hrs.

According to one embodiment of the invention, it was found that, when TGF-β expression level is 0.63 ng/10$^5$ cell/24 hours, significant pain relief and improvement in the cartilage structure are not effective, and therefore, TGF-β expression level of at least 0.65 ng/10$^5$ cell/24 hours is required.

An index for effectiveness of the cell therapeutic agent according to the present invention has excellent accuracy and reliability as an indicator, and therefore, can be used for determining effectiveness of an osteoarthritis therapeutic agent.

In the present invention, the term "expression level" or "secretion level" refers to a level of expression of TGF-β protein.

In the present disclosure, the term "determination of effectiveness" is used to refer to potential for beneficial or adverse response to therapeutic effects of the cell therapeutic agent of the present invention. In the present invention, the above determination relates to a degree of such responses. For example, effectiveness determination relates to whether treatment effects upon osteoarthritis are obtained or not and/or probability thereof after treatment using the cell therapeutic agent.

According to a preferred embodiment of the present invention, the inactivation in step (3) is performed by irradiation, wherein the irradiation may include gamma ray, x-ray or electron ray, but it is not limited thereto. Further, the irradiation may be easily conducted using various techniques known in the related art.

According to a preferred embodiment of the present invention, the vial in step (2) may contain a cryoprotective solution, wherein the cryoprotective solution includes dimethyl sulfoxide (DMSO).

Preferably, the cryoprotective solution may contain 5 to 15% by volume of DMSO.

Further, the inactivation in step (3) may be performed before or after freezing the vial, and the freezing may be performed at −20 to −196° C.

The cultivation in step (4) may be conducted after thawing the frozen vial, and the thawing may be conducted to leave the frozen vial at 15 to 40° C. for 1 to 90 minutes.

The cultivation in step (4) may be conducted for 6 to 96 hours.

According to a preferred embodiment of the present invention, the mammalian cell may be a chondrocyte or a chondroprogenitor cell.

In addition, the present invention may further include identifying an expression of TSP-1 gene in the second population. For example, normal chondrocytes, chondroprogenitor cells or stem cells are known to express TSP-1. In one embodiment of the present invention, it was found that the presence or absence of TSP-1 expression plays an important role in therapeutic effects of the cell therapeutic agent including the second population.

Accordingly, it is possible to identify whether or not expression of TSP-1 gene is present by detecting a product of the same gene in the second population, that is, RNA or protein, and to evaluate effectiveness of the second population.

As a criterion for determining the effectiveness of the cell therapeutic agent of the present invention, TSP-1 expression level in the second population is not particularly limited as far as desired effects are achieved, however, is preferably at least 31 ng/10$^5$ cells/24 hours, more preferably at least 50 ng/10$^5$ cells/24 hours and, most preferably 90 ng/10$^5$ cells/24 hrs.

In one embodiment of the present invention, it was found that no significant pain relief and improvement in the cartilage structure are exhibited when TSP-1 expression level is 30.53 ng/10$^5$ cells/24 hours, and therefore, TSP-1 expression level of at least 31 ng/10$^5$ cells/24 hours are required.

According to one embodiment of the present invention, it is determined that the cell therapeutic agent has therapeutic effects for osteoarthritis if it is detected (identified) that, among the cell therapeutic agents including: (a) a first population of mammalian cells transformed with TGF-β; and (b) a second population of mammalian cells not transformed with the same gene, wherein TGF-β expression level in the first population is 0.65 ng/10$^5$ cells/24 hours or more, while TSP-1 expression level in the second population is 31 ng/10$^5$ cells/24 hours or more.

The detection may be usually performed by extracting RNA or protein from a sample and detecting a specific part of the RNA or protein in the extract. The detection of such RNA or protein may be determined by immunoassay, hybridization and amplification, but it is not limited thereto, and may be easily conducted using various techniques known in the related art.

A detecting agent used herein may be selected from the group consisting of an antisense oligonucleotide specific to the above gene, a primer pair, a probe and a combination thereof. That is, the detection of a nucleic acid may be performed by amplification using one or more oligonucleotide primers hybridized to a nucleic acid molecule encoding a gene or a complementary molecule of the nucleic acid molecule.

For instance, the detection of a nucleic acid using a primer may be performed by amplifying a gene sequence according to an amplification process such as a polymerase chain reaction (PCR), and then determining whether the gene was amplified or not by any method known in the related art.

Further, the detecting agent may be an antibody specifically bound to an amino acid region in the protein, and may include a polyclonal antibody, a monoclonal antibody, a recombinant antibody or a combination thereof.

Such antibodies may include not only a polyclonal antibody, a monoclonal antibody, a recombinant antibody and complete form having 2 full-length light chains and 2 full-length heavy chains but also functional fragments of an antibody molecule, for example, Fab, F (ab'), F(ab')2 and Fv. Production of an antibody may be easily conducted using techniques widely known in the related art, and commercially available antibodies may also be used.

Further, according to another aspect of the present invention, there is provided a method for manufacturing an osteoarthritis therapeutic agent, which includes:

(1) preparing (a) a first population of transformed mammalian cells with TGF-β, and (b) a second population of untransformed mammalian cells with the same gene, respectively;

(2) filling the first and second populations in step (1) in a cryoprotective solution in a vial, respectively;

(3) inactivating the first population in step (2) before or after freezing the vial;

(4) thawing the first population in step (3);

(5) culturing the first population in step (4);

(6) measuring an expression level of TGF-β in the first population in step (5); and (7) selecting cells having TGF-β expression level of 0.65 ng/$10^5$ cells/24 hours or more, as measured in step (6).

According to a preferred embodiment of the present invention, the method further includes step (8) of measuring an expression level of TSP-1 in the second population, and selecting cells having TSP-1 expression level of 31 ng/$10^5$ cells/24 hours or more.

In the other words, the method of the present invention may include: selecting cells in which TGF-β expression level in the first population is 0.65 ng/$10^5$ cells/24 hours or more, and TSP-1 expression level in the second population is 31 ng/$10^5$ cells/24 hours or more; and determining the cells which are effective as a therapeutic agent, thereby preparing the therapeutic agent.

The manufacturing method of an osteoarthritis therapeutic agent according to the present invention has a configuration wherein effectiveness is determined on the basis of TGF-β and/or TSP-1 expression level(s) in: (a) a first population of transformed mammalian cells with TGF-β; and (b) a second population of untransformed mammalian cells with the same gene, respectively. In this regard, the description regarding duplicated contents will not be described in order to avoid excessive complexity of the present disclosure.

Advantageous Effects

When using (a) TGF-β expression level in the first population of transformed mammalian cells with TGF-β; and (b) TSP-1 expression level in the second population of untransformed mammalian cells with the same gene, respectively, as a criterion for determining effectiveness of the cell therapeutic agent according to the present invention, it is possible to definitely determine the therapeutic efficacy of each cell therapeutic agent prior to initiation of the treatment. In addition, since use of a cell therapeutic agent without therapeutic effects is avoided, undesired procedures and side effects may not be entailed.

BEST MODE

Figure 1:
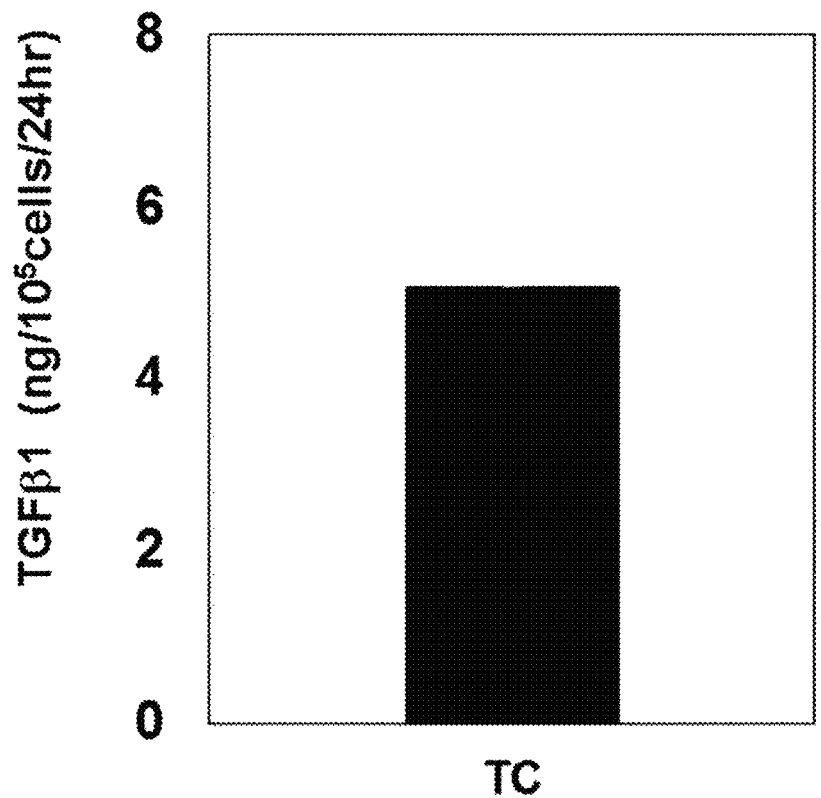
FIG. 1 is a graph illustrating an expression level of TGF-β1 protein in TC cells.

Hereinafter, the following embodiments are provided to describe the present invention in more detail. It will be apparent to those skilled in the art that the scope of the present invention in regard to the objects of invention is not limited by these embodiments.

EXAMPLE 1

Preparation of Cell Therapeutic Agent

The cell therapeutic agent used in this example of the present invention is a transformed cell population so as to express TGF-β1 (NCBI Reference Sequence: NM_000660.6) (first population; hereinafter referred to as TC) and a normal cell population without transformation using the above gene (second population; hereinafter referred to as HC).

TC could be prepared by injecting cDNA of TGF-β1 into cells according to a known method. For instance, the cDNA of TGF-β1 is inserted into a known vector having a resistant gene such as ampicillin or neomycin [for example, pCI (containing ampicillin resistant gene) from Promega Co.] to construct a vector containing cDNA of TGF-β1, followed by injecting the vector into chondrocytes according to a known method such as a calcium phosphate method or a lipofectin method, thus to prepare TC.

The HC and TC are human-derived chondrocytes, wherein HC is a normal chondrocyte while TC is a transformed chondrocyte to secrete TGF-β1. A method for construction of HC and TC has been disclosed in known documents [Cytotherapy, 2012 February; 14 (2): 247-256) and U.S. Pat. Nos. 7,005,127 and 7,282,200.

A mixing ratio of HC and TC was 3:1 based on the number of cells and was applied to the following examples.

The prepared TC and HC were filled into a vial, respectively, and frozen and prepared/stored for use as a mixed cell-based therapeutic agent. At this time, the TC was inactivated by irradiation before or after freezing.

EXAMPLE 2

Identification of TGF-β1 Secretion in Cell Therapeutic Agent

The present inventors have confirmed whether TC cells prepared according to the manufacturing process express TGF-β1 in order to establish a criterion for determining effectiveness of mixed cells as a cell therapeutic agent as in Example 1.

The TC cells were filled into a vial and inactivated in the frozen state. After inactivation, the frozen vial was taken out and thawed in a water bath at 37° C., and the cells were taken out of the vial and added in a conical tube containing a medium. The cells were centrifuged at 210×g for 5 minutes to remove supernatant. The cells were suspended in a culture medium and then inoculated into 3 wells to be $1.0 \times 10^5$ cells/well in a 6-well plate. The cells were cultured in a 37° C. $CO_2$ incubator for 24 hours, respectively.

After 24 hours, the medium was changed and the cells were cultured in a 37° C. $CO_2$ incubator for 24 hours. After incubation, the spent medium was sampled by 1 mL At this time, 2 mL of medium was used as a negative control group in 3 wells. The amount of TGF-β1 in the sampling medium was measured by ELISA method and the negative control group was also measured in the same method. TGF-β1 secretion level was calculated as "average amount of TGF-β1 secretion in the sample−average amount of TGF-β1 secretion in the negative control group."

According to the result, as shown in FIG. 1 and Table 1 below, it could be confirmed that TGF-β1 was expressed at an average of 5.07 ng/1×10⁵ cells/24 hours in TC cells.

TABLE 1

| TGF-β1 (ng/1 × 10⁵ cells/24 hours) | TC |
|---|---|
| Average | 5.07 |

EXAMPLE 3

Determination of TGF-β1 Expression Level by Batch

The expression level of TGF-β1 was examined in each manufacturing batch in order to establish TGF-β1 expression criterion which exhibits effectiveness as a cell therapeutic agent in TC cells.

Figure 2:
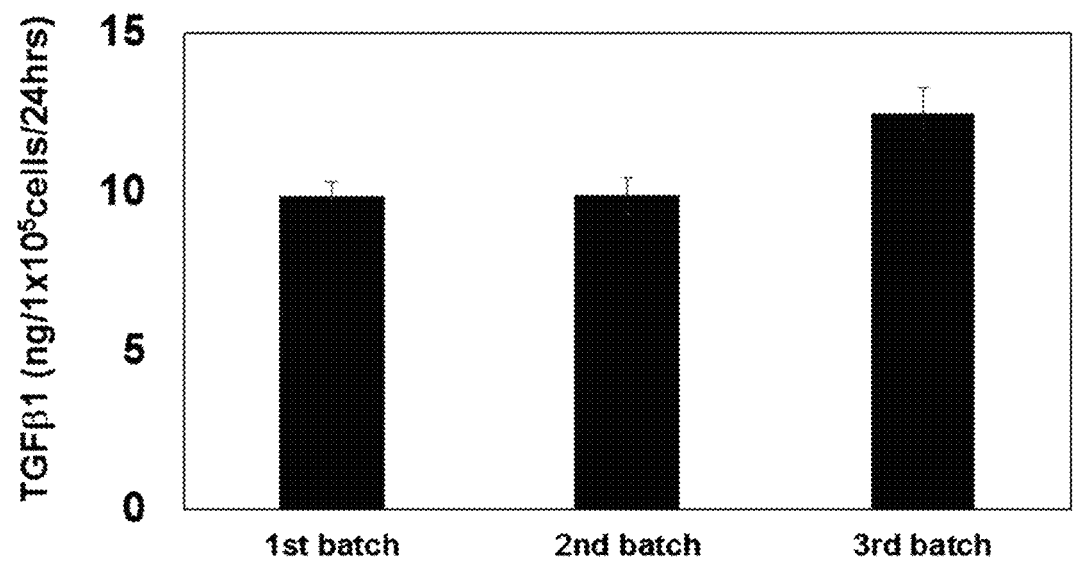
FIG. 2 is a graph illustrating the confirmed results of the expression level of TGF-β1 in each Manufacturing batch.

According to the result, as shown in FIG. 2 and Table 2 below, it could be confirmed that there was a difference in expression levels of TGF-β1 protein by batch.

TABLE 2

| TC | Batch 1 | Batch 2 | Batch 3 |
|---|---|---|---|
| TGF-β1 (ng/1 × 10⁵ cells/24 hours) | 9.86 | 9.87 | 12.46 |

As described above, since TGF-β1 protein expression level is different depending on the production batch, a greater difference may possibly occur when there is a change such as a process change. Therefore, it could be understood that a reference concentration for TGF-β1 expression should be established for quality control in regard to cell therapeutic agents capable of reproducing the same therapeutic effects.

EXAMPLE 4

Verification of Relationship Between TGF-β1 Expression and Therapeutic Efficacy in Cell Therapeutic Agent In order to verify whether there is substantially a close relationship between TGF-β1 expression level and therapeutic effects in TC cells, the present inventors have prepared an MIA osteoarthritis animal model, and then treated the model with the mixed cells and/or anti-TGF-β1 neutralizing antibody, followed by observing a change of pain.

2 weeks after the MIA injection, CS-10 administration group (vehicle) as a control group and the mixed cells ($1.2 \times 10^6$) prepared by mixing HC and TC in a ratio of 3:1 were administered, respectively, into a joint cavity of a left knee of the test animal. For neutralization antibody test, a control antibody (IgG, 500 ng/30 μL) and TGF-β1 neutralizing antibody (anti-TGF-β1, 500 ng/30 μL) were administered into the joint cavity of the left knee on the day of the mixed cell administration and on $3^{rd}$ day.

Thereafter, von Frey filament test was performed. This test was conducted using 50% up & down threshold method which was established in 1980 by Dixon (Chaplan S R et al., Quantitative assessment of tactile allodynia in the rat paw, Journal of Neuroscience Methods, 1994, 53: 55-63; and Dixon W. J., Efficient analysis of experimental observations, Annual Reviews Pharmacology Toxicology, 1980, 20: 441-62). Using a total of nine (9) von Frey filaments with N values of 0.4, 0.6, 1, 2, 4, 6, 8, and 15 grams (g), respectively, pain response was examined and a threshold value was calculated according to predetermined patterns.

Figure 3A:
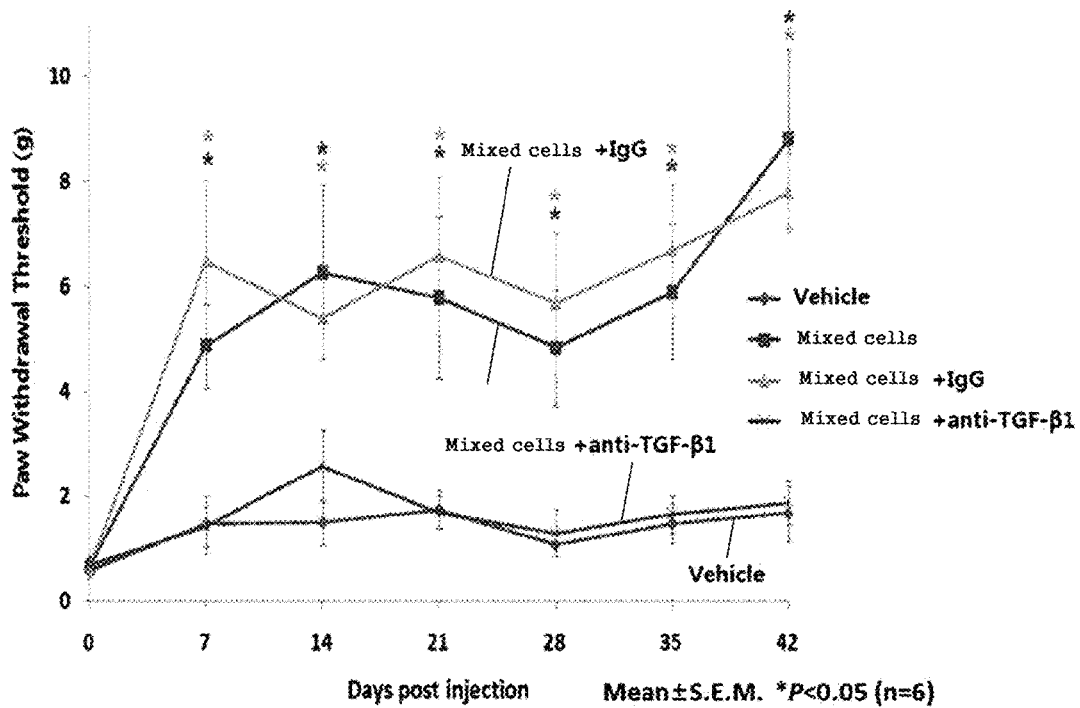
FIG. 3A is a graph illustrating von Frey filament test results when an animal model with MIA-induced osteoarthritis was treated with mixed cells and/or anti-TGF-β1 neutralizing antibody.
Figure 3B:
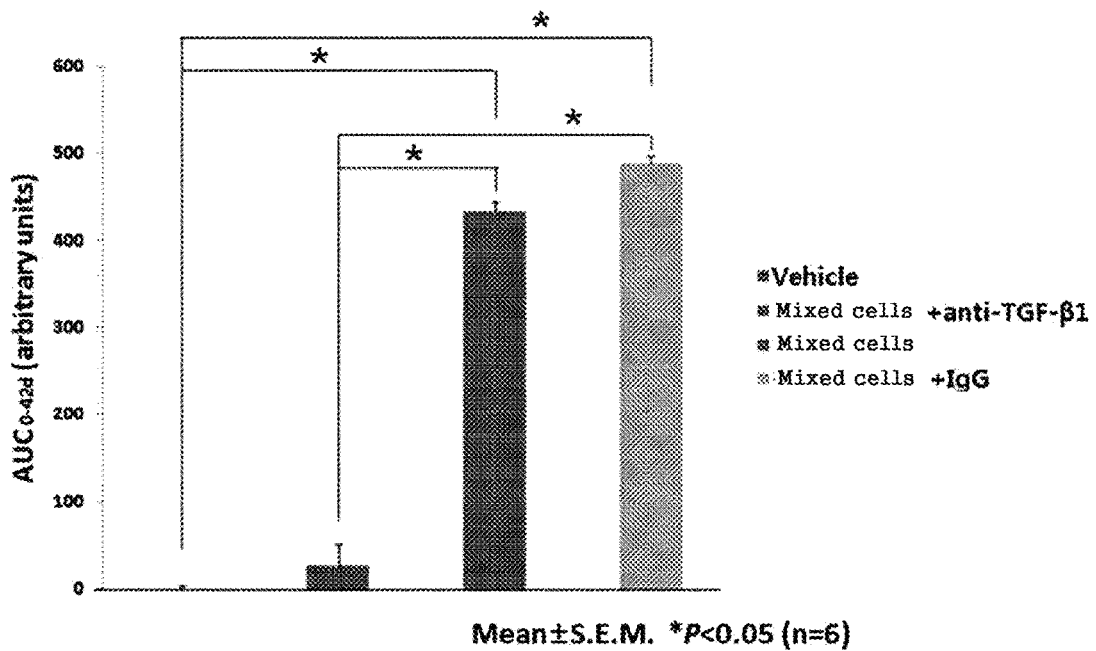
FIG. 3B is a graph illustrating the above von Frey filament test results by an area under the curve (AUC).

According to the result, as shown in FIGS. 3A and 3B, the measured results were 1.46±0.54 in the CS-10 administration group (vehicle) and 4.87±0.8 in the mixed cell administration group, respectively, on 7th day after the administration. Such analgesic effects showed a similar tendency till 42th day after the administration of cells, and as compared to the CS-10 administration group, statistically significant analgesic efficacy was observed at all measured values ($P<0.05$).

Further, in order to identify how TGF-β1 secreted by TC influences on analgesic effects in a case of the mixed cell administration, when anti-TGF-β1 neutralizing antibody which neutralizes and inhibits activity of TGF-β1 protein thus to block therapeutic effects thereof was also added, it was observed that pain therapeutic effects on the mixed cell administration group correspond to the threshold value of 1.43±0.38 in TGF-β1 neutralizing antibody administration group (mixed cell+anti-TGF-β1) on 7th day after the administration, which exhibits pain similar to that of the CS-10 administration group. Further, no difference in pain therapeutic effects was detected till 42th day. On the other hand, a group using the control antibody (IgG) (that is, mixed cells+IgG) retained pain therapeutic effects similar to the mixed cell administration group.

From the above result, it could be understood that TGF-β1 secreted from TC shows significant effects on osteoarthritis treatment.

EXAMPLE 5

Identification of TSP-1 Expression in Cell Therapeutic Agent

In order to investigate whether or not TSP-1 (NCBI Reference Sequence: NM_003246.3) protein is expressed in HC and TC cells, respectively, as well as an expression level thereof, each cell vial being stored in the same method as described in Example 2 above was thawed and TSP-1 amount was measured by ELISA method.

Figure 4:
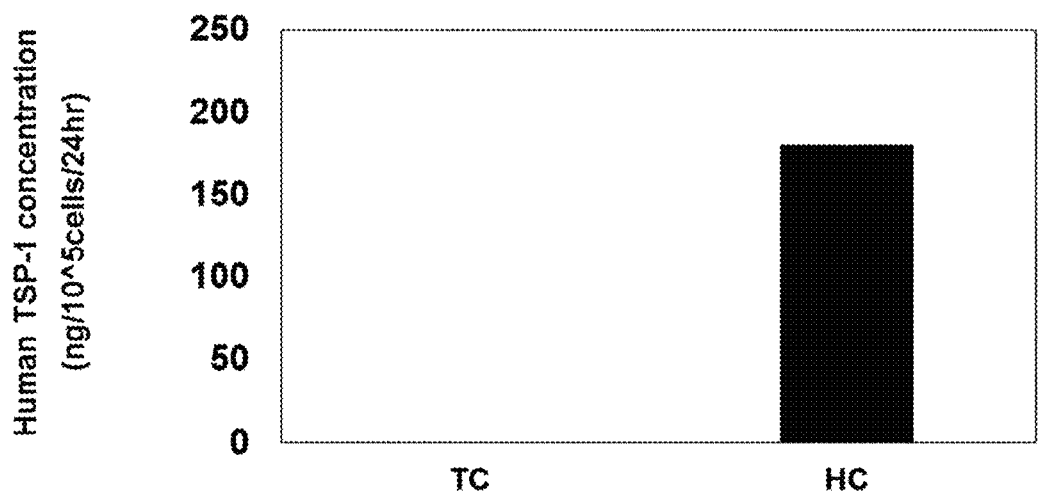
FIG. 4 is a graph illustrating the expression level of TSP-1 protein in HC cells and TC cells, respectively.

According to the result, as shown in FIG. 4 and Table 3 below, TSP-1 expression levels of 180.37 ng/1×10$^5$ cells/24 hours in HC cells and 0.29 ng/1×10$^5$ cells/24 hours were expressed TC cells, respectively, thereby demonstrating inhibition of TSP-1 expression.

TABLE 3

| TSP-1<br>(ng/1 × 10$^5$ cells/24 hours) | HC | TC |
| --- | --- | --- |
| Average | 180.37 | 0.29 |

EXAMPLE 6

Determination of TSP-1 Expression Level by Batch

The expression level of TSP-1 was examined in each manufacturing batches as described in Example 2 above in order to establish TSP-1 expression standard showing effectiveness as a cell therapeutic agent in HC cells.

Figure 5:
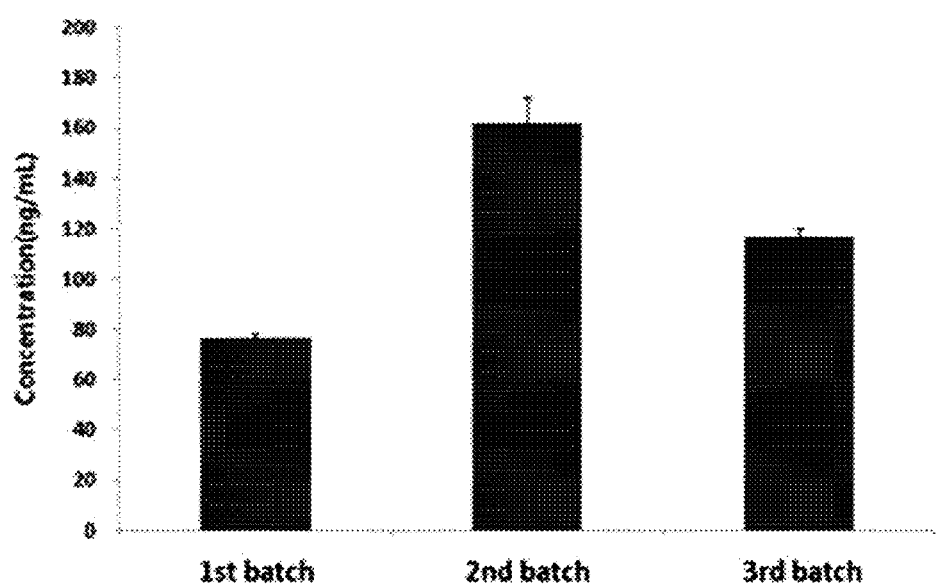
FIG. 5 is a graph and a table illustrating the confirmed results of the expression level of TSP-1 in each cell production batch.

According to the result, as shown in FIG. 5 and Table 4 below, it could be confirmed that there was a difference in expression levels of TSP-1 by batch.

TABLE 4

| HC | Batch 1 | Batch 2 | Batch 3 |
| --- | --- | --- | --- |
| TSP-1 (ng/1 × 10$^5$ cells/24 hours) | 76.41 | 162.30 | 116.14 |

As described above, since TSP-1 protein expression level is different depending on the production batch, a greater difference may possibly occur when there is a change such as a process change. Therefore, it could be understood that a reference concentration for TSP-1 expression should be established for quality control in regard to cell therapeutic agents capable of reproducing the same therapeutic effects.

Example 7

Verification of Relationship Between TSP-1 Expression and Therapeutic Efficacy in Cell Therapeutic Agent In order to verify therapeutic effects of the mixed cells, the present inventors have prepared an MIA osteoarthritis animal model in the same manner as described in Example 4 above, and then treated the model with the mixed cells and/or anti-TSP-1 neutralizing antibody, followed by observing a change of pain.

Figure 6A:
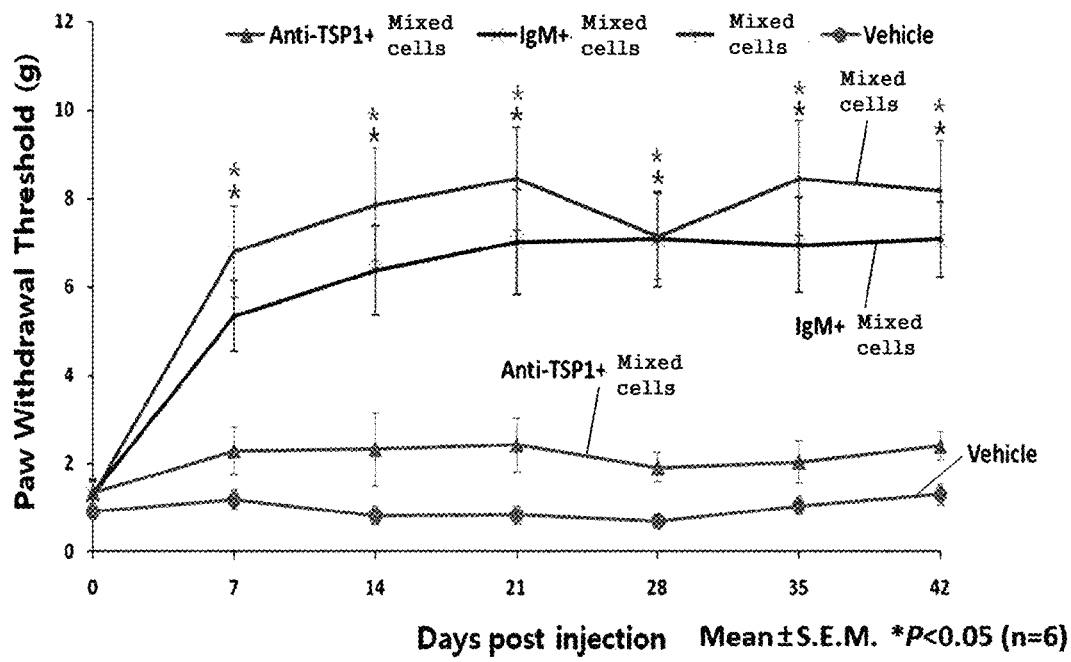
FIG. 6A is a graph illustrating von Frey filament test results when the MIA-induced osteoarthritis animal model was treated with mixed cells and/or anti-TSP-1 neutralizing antibody.
Figure 6B:
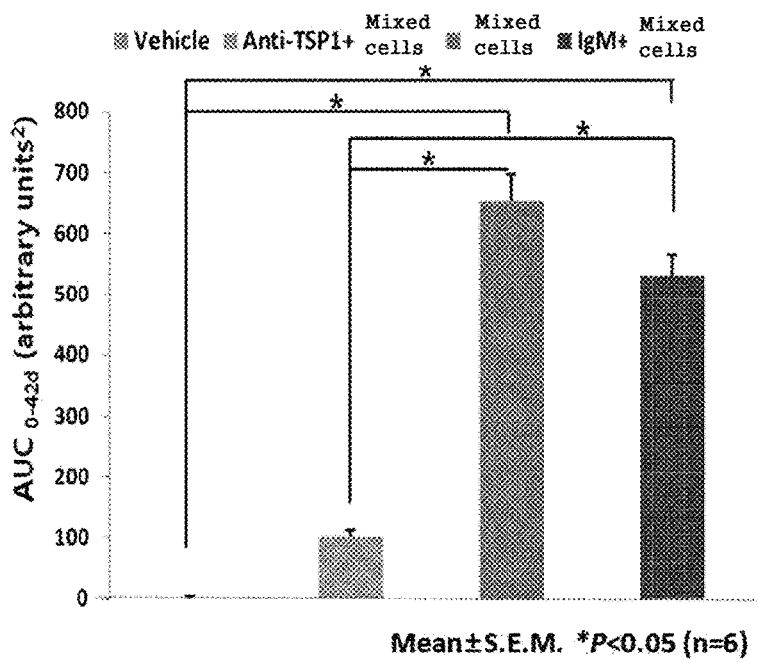
FIG. 6B is a graph illustrating the above von Frey filament test results by an area under the curve (AUC).

According to the result, as shown in FIGS. 6A and 6B, the measured results were 1.19±0.23 in the CS-10 administration group (vehicle) and 6.79±1.03 in the mixed cell administration group, respectively, on 7th day after the administration. Such pain therapeutic effects showed a similar tendency till 42th day after the mixed cell administration, and as compared to the CS-10 administration group, statistically significant analgesic efficacy was observed at all measured values (P<0.05).

Further, in order to identify how TSP-1 secreted by HC influences on analgesic efficacy of mixed cells in a case of the mixed cell administration, when anti-TSP-1 neutralizing antibody which neutralizes and inhibits activity of TSP-1 protein thus to block therapeutic effects thereof was also added, it was observed that pain therapeutic effects on the mixed cell administration group correspond to the threshold value of 2.28±0.54 in TSP-1 neutralizing antibody administration group (mixed cell+anti-TSP-1) on 7th day after the administration, which exhibits pain similar to that of the CS-10 administration group. Further, no difference in pain therapeutic effects was detected till 42 days. On the other hand, a group using the control antibody (IgM) (that is, mixed cells+IgM) exhibited pain therapeutic effects similar to the mixed cell administration group (p<0.05).

From the above result, it could be understood that TSP-1 secreted from HC shows significant effects on osteoarthritis treatment.

EXAMPLE 8

Verification of Minimum Dosage of TGF-β1 in Cell Therapeutic Agent

In order to determine a minimum value of TGF-β1 in TC which is a constitutive cell of mixed cells, the present inventors have used TCs showing different TGF-β1 values for osteoarthritis-induced subjects 2 weeks after MIA injection and treated the subjects with mixed cells (2.8×10$^5$ cells) which were prepared by mixing HCs and TCs in a ratio of cells of 3:1, followed by observing a change of pain.

At this time, in order to embody a situation of TCs having different TGF-β1 expression levels under influence of different conditions, TCs having different TGF-β1 values were prepared. Such TCs were prepared by shRNA treatment of TGF-β1 and 150 Gy gamma irradiation, and TGF-β1 average (ng/1×10$^5$ cells/24 hours) were determined as shown in Table 5 below.

TABLE 5

|  | TC | shRNA control | shRNA | 150 Gy |
| --- | --- | --- | --- | --- |
| TGF-β1 (ng/1 × 10$^5$ cells/24 hours) | 21.71 | 7.00 | 0.35 | 0.63 |

Figure 7A:
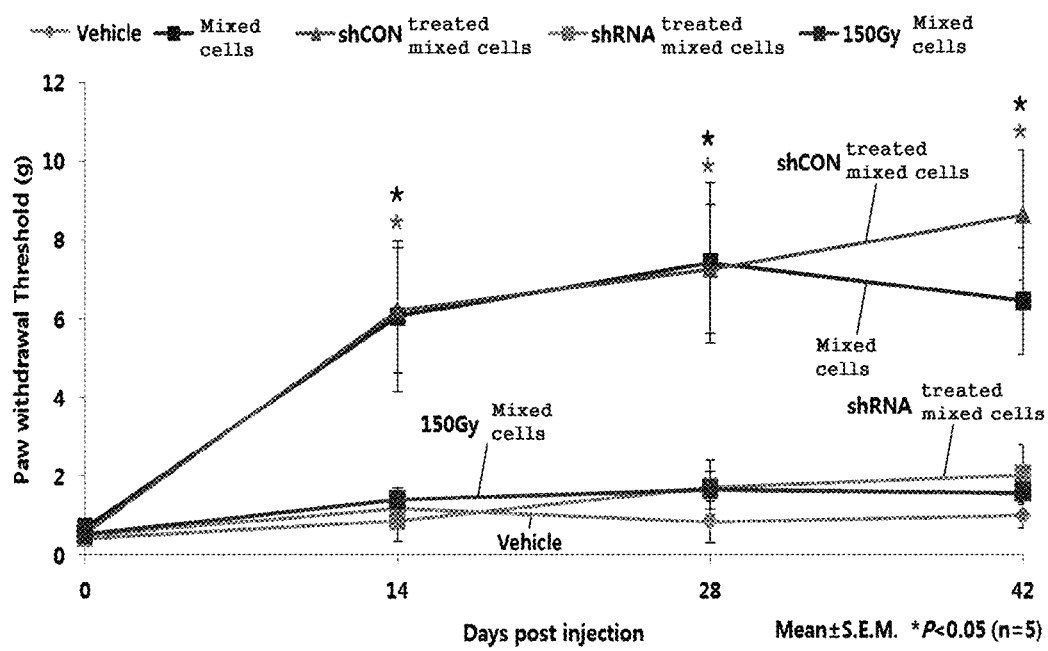
FIG. 7A is a graph illustrating von Frey filament test results when an animal model with MIA osteoarthritis was treated with mixed cells having different TGF-β1 expression levels.
Figure 7B:
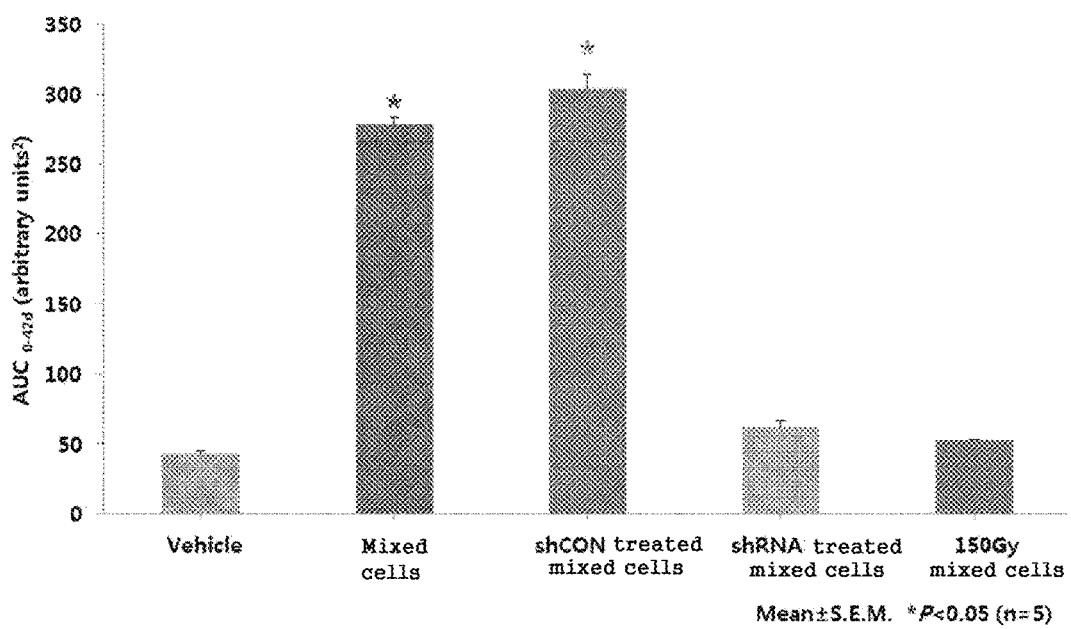
FIG. 7B is a graph illustrating the above von Frey filament test results by an area under the curve (AUC)

According to the result, as shown in FIGS. 7A and 7B, the measured results of CS-10 administration group (vehicle) and the mixed cell administration group were 1.17±0.53 and 6.06±1.91, respectively, on 14th day after the administration. Such pain therapeutic effects showed a similar tendency till 42th day after the administration of cells, and as compared to the CS-10 administration group, statistically significant analgesic efficacy was observed at all measured values (P<0.05).

Further, on the 14th day after the administration of cells, the measured results were obtained as follows: 6.21±1.59 for the shRNA control (shCON) treatment administration group; 1.39±0.23 for the mixed cell administration group using 150 Gy gamma-irradiated TC; and 0.86±0.49 for the mixed cell administration group along with shRNA treatment to TGF-β1, respectively. These effects were similar till 42th day after the administration of cells.

When von Frey filament measurement results were expressed as AUC values, statistically significant results were also demonstrated in the mixed cell administration group and the shRNA control (shCON) treatment administration group, as compared to the control group, i.e., the CS-10 administration group (p<0.05).

Figure 7C:
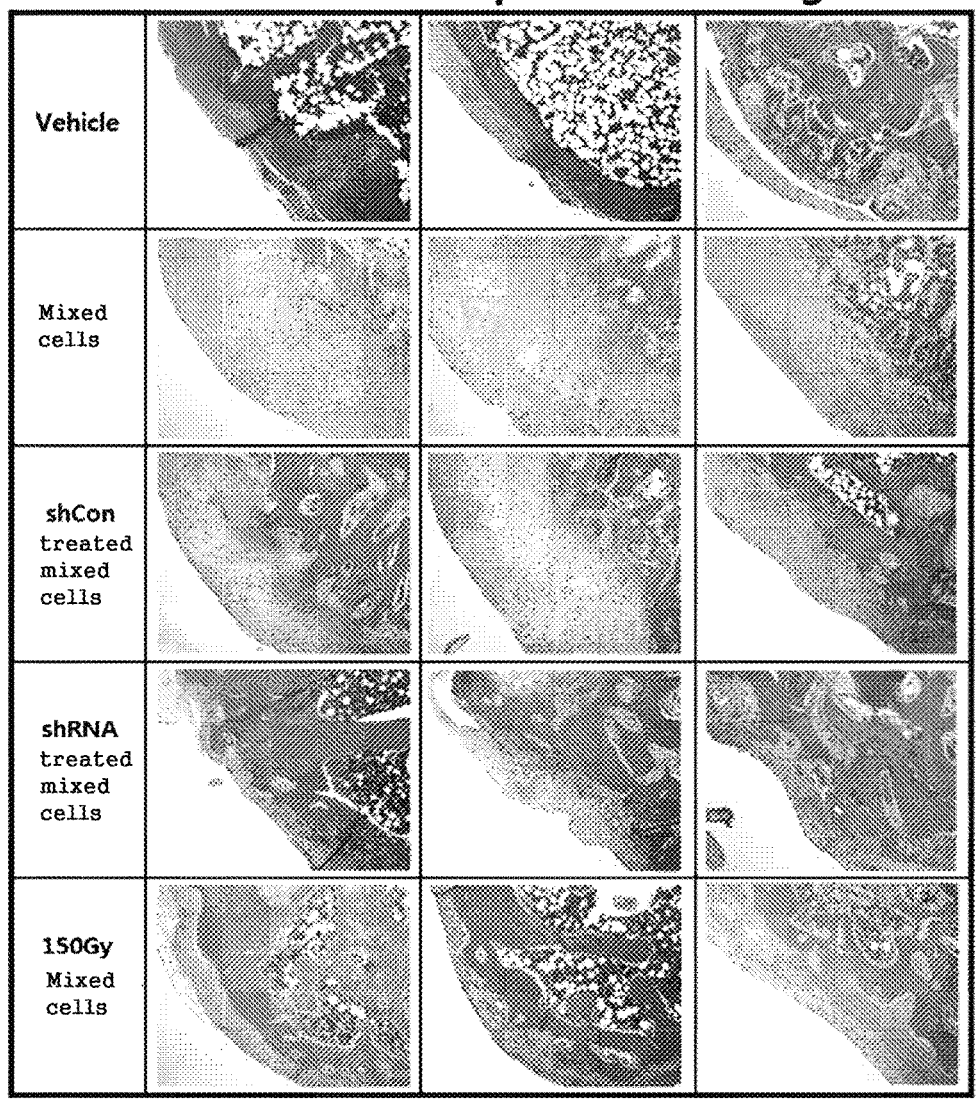
FIG. 7C are photographs illustrating results of H & E staining tissue analysis.

According to the result of H & E staining analysis for tissues isolated from the same animal model, improvement in the cartilage structure was observed in the mixed cell administration group and the shCON treatment administration group, as shown in FIG. 7C.

On the other hand, no improvement in the cartilage structure was observed in the CS-10 administration group (vehicle) as the control group, the mixed cell administration group along with shRNA treatment to TGF-β1 and the mixed cell administration group using 150 Gy gamma-irradiated TC, respectively.

In addition, in order to determine a minimum effective value for pain relief by TGF-β1 secreted from TC as well as cartilage structure improvement, analgesic effects and improvement in the cartilage structure by mixed cells using TC produced in another batch were examined.

TGF-β1 values of the prepared TC were 9 ng/1×10$^5$ cells/24 hours and 1.7 ng/1×10$^5$ cells/24 hours, respectively. These TCs were used in preparation of the mixed cells. The prepared mixed cells were indicated as 9 ng_mixed cells and 1.7 ng_mixed cells, respectively.

Figure 8A:
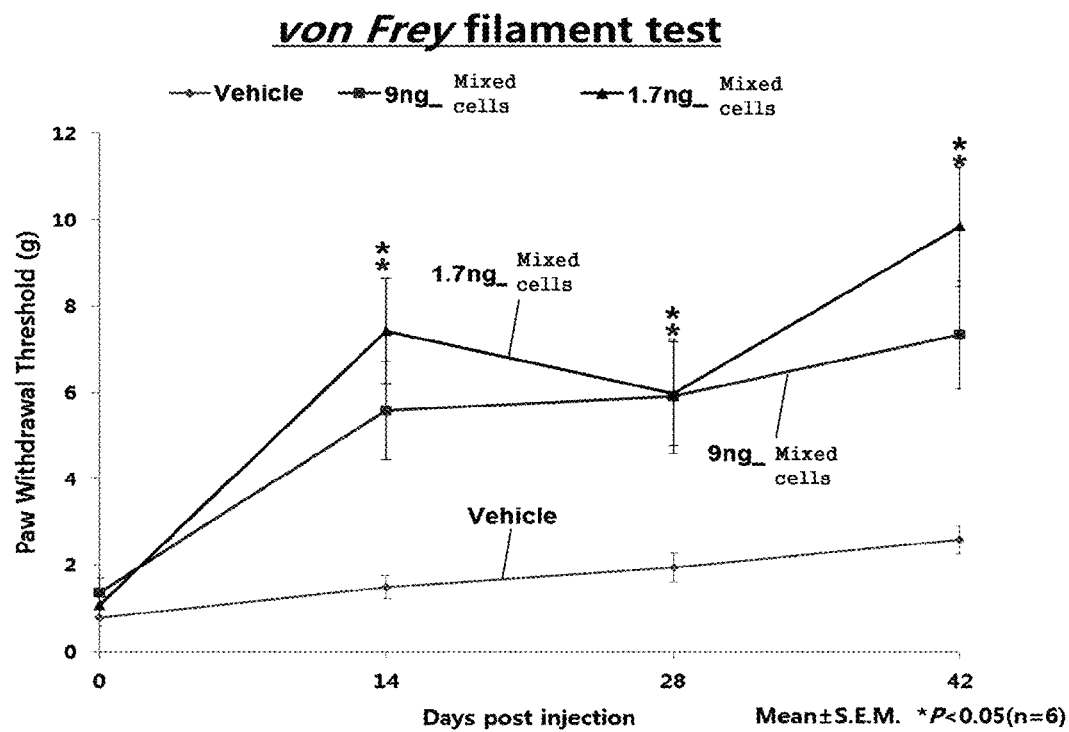
FIG. 8A a graph illustrating 1, 2 VFF test results of 120 Gy mixed cells in order to determine minimum effective value of TGF-β1.
Figure 8B:
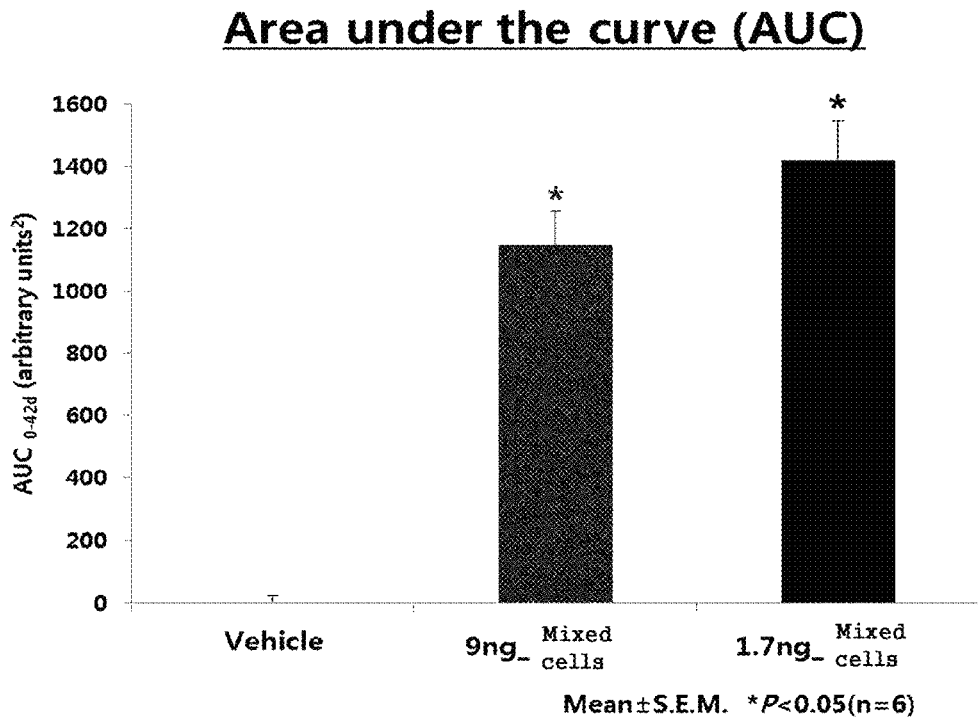
FIG. 8B a graph illustrating the counted results by AUC.

According to the result, as shown in FIGS. 8A and 8B, on 14th day after the administration of 9 ng_mixed cells, 1.7 ng_mixed cells and CS-10 administration group (vehicle) as the control group, respectively, the measured results were as follows: 1.48±0.26 for the CS-10 administration group; 5.57±1.13 for 9 ng mixed cells; and 7.41±1.21 for 1.7 ng_mixed cells. There was a similar tendency till 42th day after the administration of cells. In comparison with the CS-10 administration group, both of 9 ng_mixed cell and 1.7 ng_mixed cell administration groups showed statistical significance (P<0.05).

When von Frey filament measurement results were expressed as AUC values, statistically significant results were also demonstrated in the 9 ng mixed cell and 1.7 ng_mixed cell administration groups, as compared to the control group, i.e., the CS-10 administration group (p<0.05).

Therefore, in the results obtained after the administration of mixed cells using different TGF-β1s secreted from TC, the minimum effective values of TGF-β1 for pain relief and improvement in the cartilage structure were measured to be higher than 0.63 ng/1×10$^5$ cells/24 hours determined in the 150 Gy gamma-irradiated mixed cell administration group, i.e., 0.65 ng/1×10$^5$ cells/24 hours or more.

EXAMPLE 9

Verification of Minimum Dosage of TSP-1 in Cell Therapeutic Agent

In order to determine a minimum value of TSP-1 in HC which is a constituent cell of mixed cells, the present inventors have treated osteoarthritis-induced subjects 2 weeks after MIA injection with mixed cells (2.8×10$^5$), which were prepared by mixing HCs and TCs in a ratio of 3:1, wherein HCs exhibit different TSP-1 values for the subjects, followed by observing a change of pain.

At this time, in order to embody HC situation different in TSP-1 expression levels due to different conditions, HCs exhibiting different expression levels of TSP-1 were prepared.

Such HCs with different TSP-1 values were prepared using siRNA to TSP-1, and average TSP-1 values (ng/1×10$^5$ cells/24 hours) were determined as shown in Table 6 below.

TABLE 6

|  | HC | siRNA control | siRNA 1 | siRNA 2 |
| --- | --- | --- | --- | --- |
| TSP-1 (ng/1 × 10$^5$ cells/24 hours) | 349.03 | 200.09 | 92.13 | 30.53 |

Figure 9A:
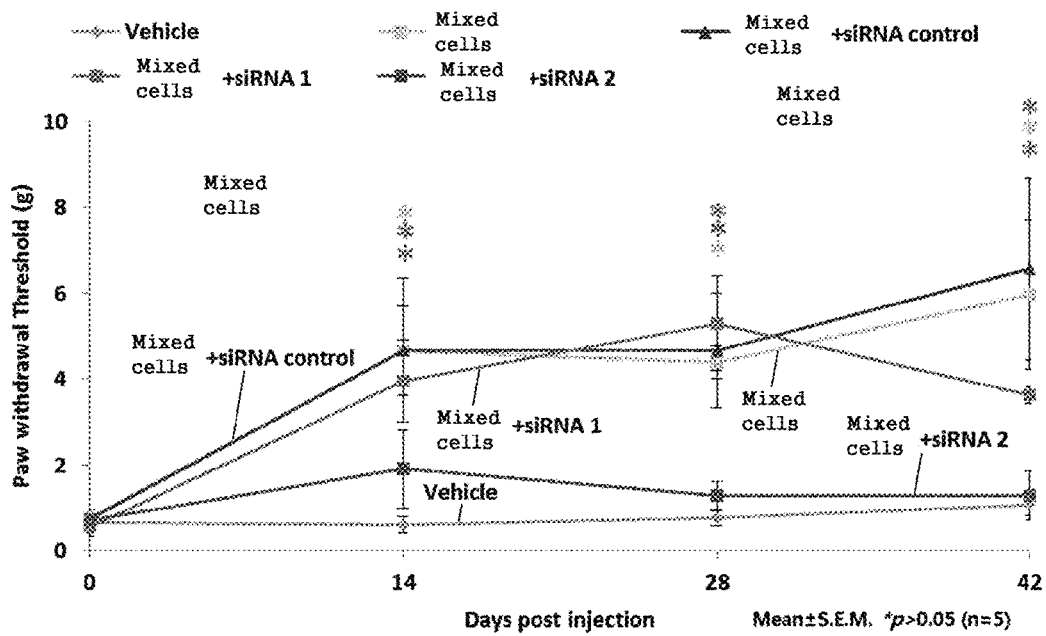
FIG. 9A a graph illustrating 1, 2 VFF test results of 120 Gy mixed cells in order to determine minimum effective value of TSP-1.
Figure 9B:
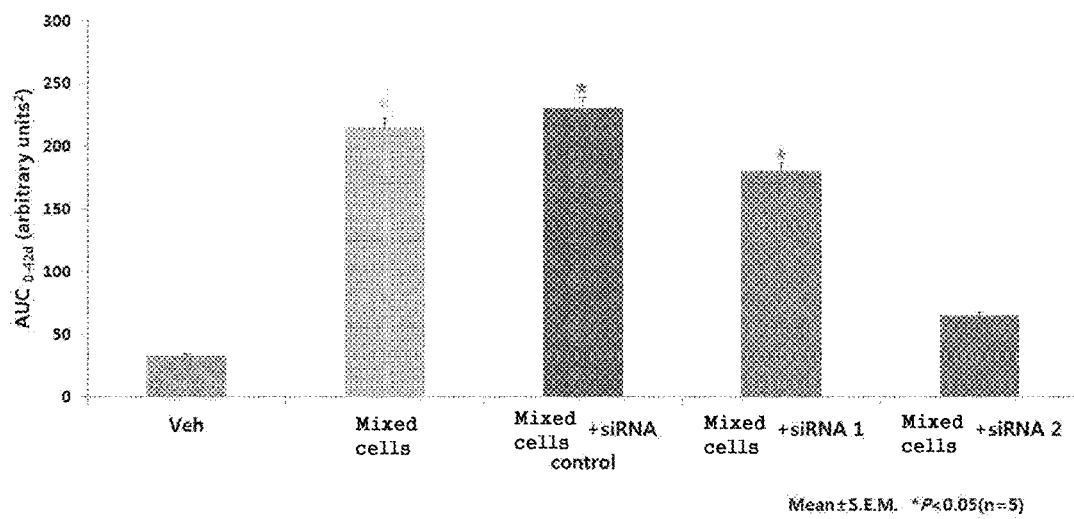
FIG. 9B a graph illustrating counted results by AUC.

According to the result, as shown in FIGS. 9A and 9B, the measured results were as follows: 0.6±0.19 for the CS-10 administration group (vehicle); 4.7±1.03 for the mixed cell administration group; and 4.7±1.67 for the mixed cell+siRNA control administration group, respectively, on 14th day after the administration. Such effects showed a similar tendency till 42th day after the administration of cells, and as compared to the CS-10 administration group, statistically significant analgesic efficacy was observed at all measured values (P<0.05).

Further, on 14th day after the administration, the measured results for the mixed cell+siRNA 1 administration group and the mixed cell+siRNA 2 administration group were 3.95±0.94 and 1.89±0.9, respectively. As compared to the CS-10 administration group, statistically significant analgesic efficacy was observed in the mixed cell+siRNA 1 administration group. These pain therapeutic effects have a similar tendency till 42th day after the administration of cells.

When von Frey filament measurement results were expressed as AUC values, statistically significant results were also obtained in the mixed cell administration group, the siRNA control treatment administration group and the mixed cell+siRNA 1 administration group, respectively, as compared to the control group, i.e., CS-10 administration group (vehicle) (P<0.05).

Figure 9C:
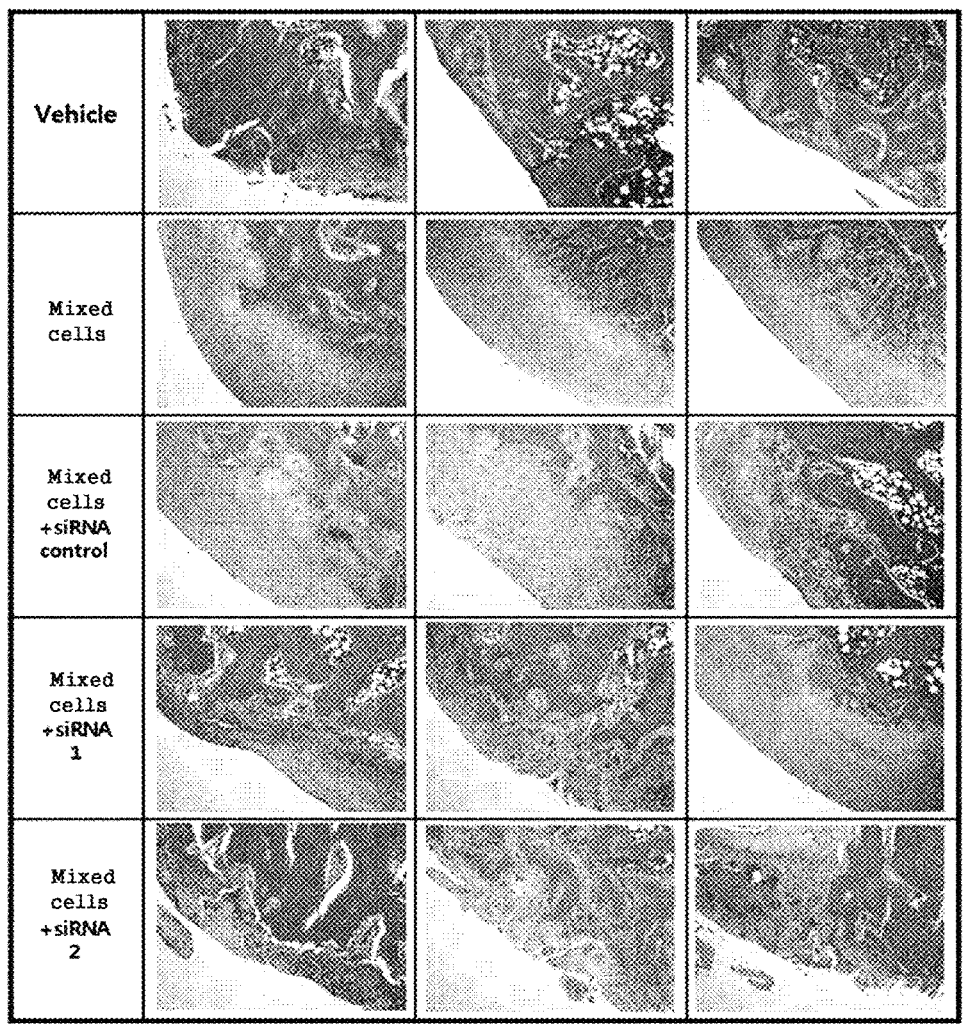
FIG. 9C are photographs illustrating results of H & E staining tissue analysis.

In addition, according to the result of H & E staining analysis for tissues isolated from the same animal model, as shown in FIG. 9C, improvements in the cartilage structure were observed in the mixed cell administration group, the siRNA control treatment administration group and the mixed cell+siRNA 1 administration group. On the other hand, for the CS-10 administration group (vehicle) as the control group and the mixed cell+siRNA 2 administration group, no improvement in the cartilage structure was observed.

Therefore, it was determined that the minimum effective value for pain relief and improvement in the cartilage structure of TSP-1 secreted from HC was higher than 30.53 ng/1×10$^5$ cells/24 hours, which was determined in the mixed cell+siRNA 2 administration group, specifically, 31 ng/1×10$^5$ cells/24 hours or more.

In conclusion, when using the method for evaluating effectiveness of an osteoarthritis therapeutic agent established according to the present invention, based on: (a) a specific TGF-β expression level in transformed mammalian cells with TGF-β as a first population; and (b) a specific TSP-1 expression level in untransformed mammalian cells with the same gene as a second population, effectiveness (i.e., therapeutic efficacy) of individual cell therapeutic agents can be reliably determined prior to initiation of treatment, thereby accomplishing uniform therapeutic effects.

The invention claimed is:

1. A method for evaluating effectiveness of a cell therapeutic agent, comprising:
    (1) preparing (a) a first population of transformed mammalian cells with a transforming growth factor beta (TGF-β), and (b) a second population of untransformed mammalian cells with the same gene, respectively;
    (2) filling the first and second populations resulting from step (1) into individual vials;
    (3) inactivating the first population resulting from step (2);
    (4) culturing the first population resulting from step (3);
    (5) measuring a concentration of TGF-β from the first population resulting from step (4);
    (6) evaluating effectiveness of a cell composition comprising the first population and the second population as a therapeutic agent based on the TGF-β concentration measured in step (5), wherein, if an expression level of TGF-β is 0.65 ng/$10^5$ cells/24 hours or more in step (6), it is determined that the cell composition is effective as a therapeutic agent; and
    determining an expression level of thrombospondin 1 (TSP-1) in the second population.

2. The method according to claim 1, wherein the inactivation in step (4) is performed by irradiation.

3. The method according to claim 2, wherein the irradiation includes gamma ray, x-ray or electron ray.

4. The method according to claim 1, wherein the vial in step (2) contains a cryoprotective solution.

5. The method according to claim 4, wherein the cryoprotective solution in step (2) includes dimethyl sulfoxide (DMSO).

6. The method according to claim 5, wherein the cryoprotective solution in step (2) contains 5 to 15% by volume of DMSO.

7. The method according to claim 1, wherein the inactivation in step (3) is performed before or after freezing the vial.

8. The method according to claim 7, wherein the freezing is performed at −20 to −196° C.

9. The method according to claim 7, wherein the cultivation in step (4) is performed after thawing the frozen vial.

10. The method according to claim 9, wherein the thawing is to leave the frozen vial at 15 to 40° C. for 1 to 90 minutes.

11. The method according to claim 1, wherein the cultivation in step (4) is performed for 6 to 96 hours.

12. The method according to claim 1, wherein the method further comprises administering the therapeutic agent to treat osteoarthritis.

13. The method according to claim 1, wherein, if the expression level of TSP-1 is 31 ng/$10^5$ cells/24 hours or more, it is determined that the cell composition is effective as a therapeutic agent.

14. The method according to claim 1, wherein the second population of the untransformed mammalian cell is a chondrocyte or chondroprogenitor cell.

* * * * *